United States Patent [19]

Kita et al.

[11] Patent Number: 4,851,547

[45] Date of Patent: Jul. 25, 1989

[54] METHOD FOR PRODUCTION OF MALEIMIDES

[75] Inventors: Yuichi Kita, Akashi; Koichi Nakagawa, Himeji; Kentaro Sakamoto, Ibo; Akio Fukui, Kamakura; Masao Baba, Himeji; Yoichi Nakagawa, Takarazuka, all of Japan

[73] Assignee: Nippon Shokubai Kagaku Kogyo Co., Ltd., Osaka, Japan

[21] Appl. No.: 289,237

[22] Filed: Dec. 23, 1988

Related U.S. Application Data

[63] Continuation-in-part of Ser. No. 79,120, Jul. 29, 1987, abandoned.

[30] Foreign Application Priority Data

Jul. 31, 1986 [JP] Japan ................... 61-178768
Sep. 25, 1986 [JP] Japan ................... 61-224839
Jun. 25, 1987 [JP] Japan ................... 62-156619

[51] Int. Cl.$^4$ ........................... C07D 207/40
[52] U.S. Cl. ..................... 548/548; 546/167; 546/281; 548/546; 548/547; 548/549
[58] Field of Search ............... 548/548, 549, 546, 547; 546/167, 281

[56] References Cited

U.S. PATENT DOCUMENTS

| | | | |
|---|---|---|---|
| 2,444,536 | 7/1948 | Searle | 548/548 X |
| 3,018,292 | 1/1962 | Sauers et al. | 548/548 |
| 3,431,276 | 3/1969 | Nield | 548/548 X |
| 3,960,887 | 6/1976 | Renard | 548/548 X |
| 4,171,302 | 10/1979 | Abblard et al. | 548/548 X |
| 4,229,351 | 10/1980 | Kiefer et al. | 548/548 X |
| 4,623,734 | 11/1986 | Kita et al. | 548/548 |

FOREIGN PATENT DOCUMENTS

| | | | |
|---|---|---|---|
| 0129125 | 12/1984 | European Pat. Off. | |
| 1269126 | 1/1969 | Fed. Rep. of Germany | |
| 0109562 | 6/1985 | Japan | 548/548 |
| 2002378 | 2/1979 | United Kingdom | |

Primary Examiner—Joseph Paul Brust
Attorney, Agent, or Firm—Omri M. Behr,

[57] ABSTRACT

A method for the production of a maleimide by dehydration and ring-closure of maleinamic acid obtained by the reaction of maleic anhydride with an amine, which method is characterized by effecting ring-closure imidation of said maleinamic acid by heating said maleinamic acid in a water-insoluble or water-immiscible inert organic non-polar solvent in the presence of a catalyst of an amine salt produced from the amine and an acid, a mixture of the amine salt and the acid, or a supported catalyst on a solid carrier the catalyst or the acid.

12 Claims, No Drawings

METHOD FOR PRODUCTION OF MALEIMIDES

This is a continuation-in-part of copending application Ser. No. 079,120, filed July 29, 1987, which is now abandoned.

BACKGROUND OF THE INVENTION

1. Field of the Invention:

This invention relates to a method for the production of maleimides. More particularly, this invention relates to a method for the production of maleimides by ring-closure imidation of maleinamic acids.

2. Description of the Prior Art:

Maleimides are compounds useful as raw materials for synthetic resins, medicines, and agricultural chemicals. Researches after methods for their produciton have long been under way. The most popular method of them all effects the production of maleimides by the dehydration cyclization of maleinamic acids with a dehydrating agent such as acetic anhydride. One version of this method is disclosed in U.S. Pat. No. 2,444,536. This method effects the production of maleimides by causing maleic anhydride to react upon amines thereby forming maleinamic acids and dehydration cyclizing and, at the same time, imidating the maleinamic acids in the presence of acetic anhydride and sodium acetate. This method, however, has the disadvantage that the imidation requires expensive acetic anhydride to be used in at least an equivalent relative to the maleinamic acid and the separation and recovery of the formed maleimide from the imidation reaction solution necessitates use of a large volume of water and, as the result, entails disposal of a large amount of an acetic acid-containing effluent at great expense. Thus, this method may will be called a too expensive method for commercial production of maleimdies.

A method which has no use for such a chemical dehydration agent as acetic anhydride is disclosed in British Pat. No. 1,041,027 and U.S. Pat. No. 3,431,276. This method effects the production of maleimides by thermally dehydrating and cyclizing maleinamic acids in conjunction with a solvent such as, for example, toluene, xylene, or chlorobenzene having a boiling point exceeding 80° C. and serving as a diluent and an acid catalyst such as sulfur trioxide, sulfuric acid, or orthophosphoric acid, and distilling the system thereby causing azeotropic expulsion of the consequently formed water in conjunction with the solvent. As compared with the method which uses acetic anhdyride, this method proves advantageous in that it does not require use of a large amount of such an expensive dehydrating agent as acetic anhydride and further that the formed maleimides are separated and recovered with ease. This method nevertheless has the disadvantage that the yield of the imidation is low as compared with that obtainable by the method using acetic anhdyride. This disadvantage is logically explained by a postulate that compared with the method which effects the imidation by the use of acetic anhydride, the method which effects the imidation by performing thermal dehydration in the specific solvent as described above involves a high reaction temperature and, therefore, tends to induce side reactions and inevitably manages to produce maleimides abounding with impurities and further that since maleimdies are thermally unstable, the maleimides produced at all are degenerated during the course of the reaction. Further, as a commercial process, this method is not ecconomically satisfactory, because it requires to use an expensive acid catalyst in a relatively large amount and, moreover, produces the maleimides in a low yield.

There is another method which, as disclosed in Japanese Patent Laid-Open No. SHO 53(1978)-68,700 and Japanese Patent Publication No. SHO 57(1978)-42,043, comprises causing maleic anhydride to react on amines in the presence of an organic solvent thereby forming maleinamic acids and subjecting the maleinamic acids as held in a state not isolated from the reaction system to dehydration and cyclization in the presence of such an aprotic polar solvent as dimethyl formamide or dimethyl sulfoxide and an acid catalyst. By this method, there is offered recognizable improvement in yield as compared with the second method described above. This method, however, has these disadvantages, that the cost of production of maleimides is high because expensive and highly toxic aprotic polar solvent such as dimethyl formamide is used in a large amount, that the solvent such as dimethyl formamide is degenerated by the action of an acid catalyst used in the reaction and, therefore, the solvent is lost greatly, and that since the aprotic polar solvent used in the reaction has a high boiling point, the solvent is removed from the produced malimides with great difficulty.

Japanese Patent Laid-Open No. SHO 54(1979)-30,155 discloses a method for producing an oligoimide by using, as a catalyst, a mixture of an inorganic or organic acid-containing acid with a quaternary ammonium salt of the acid. The quaternary ammonium salt which is used as mixed with an acid catalyst in this method, however, is an ammonium salt of the nitrogen atom of which has been at least disubstituted. Specifically, this is an expensive interphase catalyst such as dimethyldialkyl ammonium methane sulfonate or tetraoctyl ammonium methane sulfonate. The method, thus necessitating use of such a compound as indicated aobve, is inevitably judged to be an expensive approach. For this method to maintain a highly satisfactory yield of imidation, however, it is essential that the reaction should be continued with the ratio of the acid catalyst to the quaternary ammonium salt rigidly controlled within a certain range. When the catalyst which has been used once in the reaction is used again, the imidation cannot be obtained in a highly satisfactory yield because the ratio is varied in the presence of the used catalyst. An effort to attain efficient reuse of the used catalyst, therefore, entails as a problem the fact that the management for maintenance of catalytic activity as by subjecting the used catalyst to purifying and readjusting treatment calls for immense labor.

Japanese Patent Laid-Open No. SHO 60(1985)-109,562 discloses a method for the production of monomaleimide by the cyclizing imidation of maleinamic acid in a mixed solvent containing a nonpolar solvent such as toluene or xylene and a polar solvent such as dimethyl sulfoxide or N-methyl pyrrolidone in a specific ratio in the presence of an acid catalyst such as p-toluenesulfonic acid or m-toluenesulfonic acid and a mixed catalyst containing the acid catalyst and an ammonium salt such as, for example, the salt thereof with maleinamic acid. In this method, however, since the acid catalyst and the polar solvent in the mixed solvent react with each other to form a complicate complex (which is widely variable with the ratio of the amounts of the two compounds and the temperature, for example), it is the complicate catalyst system composed of the complex just mentioned, the acid, and the salt that substantially produces a catalytic activity. Thus, the yield of the imidation is affected to a great extent by the composition of the three components mentioned above. When the reaction is carried out batchwise, it does not intail any appreciable disadvantage. When the reaction is carried out in such operation system as require the catalyst and the solvent to be used in a recycling manner, however, it entails various drawbacks. To be specific, this method renders the selection of reaction conditions complicate because the amount of the complicate complex produced owing to the use of the polar solvent is varied and the catalyst is varied in quality from one batch to another. This is equivalent to a statement that the method under discussion has the disadvantage that it is unfit for a continuous reaction.

An object of this invention is to provide an improved method for the production of maleimides.

Another object of this invention is to provide a method for producing a maleimide of high purity in a high yield by a safe and simple procedure.

Yet another object of this invention is to provide a method for enabling the production of a maleimide to be effected easily by a continuous reaction.

SUMMARY OF THE INVENTION

The objects described above are accomplished by a method for the production of a maleimide of formula II:

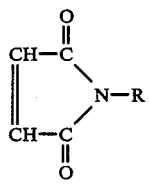
(II)

wherein R is a member selected from the group consisting of alkyl of 1-20 carbon atoms, phenyl, benzyl, cyclohexyl, pyridyl, quinolyl and the said moieties when substituted by halongen, carboxyl or nitro which comprises the sequential steps of (a) reacting maleic anhydride with a primary amine of the formula NH$_2$-R wherein R is as defined above to form the corresponding maleinamic acid and (b) heating said maleinamic acid in a water insoluble or water immiscible inert non-polar organic solvent said solvent being utilized in a ratio by volume of from about 1 to about 20 to 1 with respect to said maleinamic acid in the presece of said primary amine acid addition salt catalyst, in an amount of about 2 to about 400 mol % of acid addition component, based on said maleinamic acid, formed from said primary amine and a strong inorganic or organic acid, said salt containing said acid addition component in an amount of less than 60 mol %, at a temperature of from about 120° and 250° C. and continuously distilling off the thus formed water as a mixture with said solvent.

The objects described above are also accomplished by a method for the production of a maleimide of formula II:

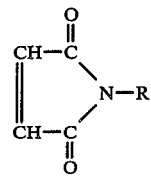
(II)

wherein R is a member selected from the group consisting of alkyl of 1-20 carbon atoms, phenyl, benzyl, cyclohexyl, pyridyl quinolyl and the said moieties when substituted by halogen, carboxyl or nitro which comprises the sequential steps of:

(a) reacting maleic anhydride with a primary amine of the formula NH$_2$-R wherein R is as defined above to form the corresponding maleinamic acid and (b) heating said maleinamic acid in a water insoluble or water immiscible inert non-polar organic solvent said solvent being utilized in a ratio by volume of from about 1 to about 20 to 1 with respect to said maleinamic acid in the presence of a catalyst supported on a solid inert organic or inorganic carrier said catalyst containing an acid component in an amount of about 2 to about 400 mol % of acid component, based on said maleinamic acid, at least one catalyst ingredient being selected from the group consisting of (a) a strong organic or inorganic acid, (b) said amine acid addition salt produced from said primary amine and a strong inorganic or organic acid, and (c) a mixture of said amine acid addition salt and a strong acid, at a temperature of from about 120° and 250° C. and continuously distilling off the thus formed water as a mixture with said solvent.

The objects described above are also accomplished by a method for the production of a maleimide of formula II:

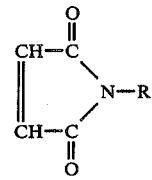
(II)

wherein R is a member selected from the group consisting of alkyl of 1-20 carbon atoms, phenyl, benzyl, cyclohexyl, pyridyl, quinolyl and the said moieties when substituted by halogen, carboxyl or nitro which comprises the sequential steps of:

(a) reacting maleic anhydride with a primary amine of the formula NH$_2$-R wherein R is as defined above to form the corresponding maleinamic acid, (b) heating said maleinamic acid in a water insoluble or water immiscible inert non-polar organic solvent, said solvent being utilized in a ratio by volume of from about 1 to about 20 to 1 with respect to said maleinamic acid in the presence of a metal containing compound selected from the group consisting of oxides, acetates, maleates, succinates, nitrates, phosphates, chlorides and sulfates of a metal selected from the group consisting of zinc, chromium, palladium, cobalt, nickel, iron and aluminum and a stabilizer selected from the group consisting of methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic ester, mercaptobenzimidazole, triphenyl phosphite, alkylphenols and alkylbisphenols, and in the presence of said primary amine acid addition salt catalyst, in an amount of about 2 to about 400 mol % of acid addition component, based on the maleinamic acid, formed from said primary amine and a strong inorganic or organic acid, the salt containing the acid addition component in an amount of less than 60 mol % at a temperature of from about 120° and 250° C. and continuously distilling off the thus formed water as a mixture with said solvent.

The objects described above are also accomplished by a method for the production of a maleimide of formula II:

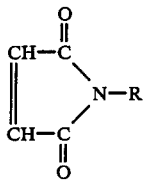

(II)

wherein R is a member selected from the group consisting of alkyl of 1-20 carbon atoms, phenyl, benzyl, cyclohexyl, pyridyl, quinolyl and the said moieties when substituted by halogen, carboxyl or nitro which comprises the sequential steps of:

(a) reacting maleic anhydride with a primary amine of the formula $NH_2$-R wherein R is as defined above to form the corresponding maleinamic acid, (b) heating said maleinamic acid in a water insoluble or water immiscible inert non-polar organic solvent, said solvent being utilized in a ratio by volume of from about 1 to about 20 to 1 with respect to said maleinamic acid in the presence of a metal containing compound selected from the group consisting of oxides, acetates, maleates, succinates, nitrates, phosphates, chlorides and sulfates of a metal selected from the group consisting of zinc, chromium, palladium, cobalt, nickel, iron and aluminum and a stabilizer selected from the group consisting of methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic ester, mercaptobenzimidazole, triphenyl phosphite, alkylphenols and alkylbisphenols, and in the presence of a catalyst supported on a solid inert organic or inorganic carrier said catalyst containing an acid component in an amount of about 2 to about 400 mol % of acid component, based on said maleinamic acid, at least one catalyst ingredient being selected from the group consisting of (a) a strong organic or inorganic acid, (b) an amine acid addition salt produced from said primary amine and a strong inorganic or organic acid, and (c) a mixture of said amine acid addition salt and a strong acid at a temperature of from about 120° and 250° C. and continuously distilling off the thus formed water as a mixture with said solvent.

We have long been continuing a study on the reactions for synthesis of maleimides. Particularly, we have devoted our study to development of a catalyst for use in the ring-closure imidation reaction. The study has resulted in a finding that an amine salt produced by the neutralization of the amine used as the raw material for the maleimide with an acid or a mixture of the amine salt with an acid manifests a catalytic activity of unusually high selectivity on the cyclizing imidation reaction. This invention has been perfected as the result.

In the light of the long cherished theory that the presence of an oxygen-containing acid is indispensable to the reaction of ring-closure imidation, it is literally an amazing fact that the use of the amine salt produced by the neutralization brings about an unusually high catalytic activity in the reaction of ring-closure imidation.

DESCRIPTION OF PREFERRED EMBODIMENTS

The method for the production of an maleimide according to this invention resides in causing dehydration and ring-closure imidation of a maleinamic acid obtained by the reaction of maleic anhydride with an amine to be carried out in a water-insoluble or water-immiscible inactive non-polar organic solvent in the presence of (a) an amine salt obtained from said amine and an inorganic or organic acid, (b) a mixture of said amine salt with the inorganic or organic acid, or (c) a catalyst produced by supporting on a solid carrier an acid or the amine salt or a mixture of the amine salt with the acid.

The maleinamic acids to be used in this invention are easily obtained generally by the reaction of primary amines with maleic anhydride. They are desired to be compounds represented by the following general formula I.

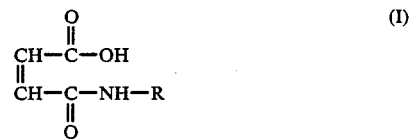

(I)

wherein R denotes a member selected from the class consisting of alkyl of 1 to 20 carbon atoms, phenyl, benzyl, cyclohexyl, pyridyl, and quinolyl groups, and the same groups as mentioned above and possessed of halogen, carboxyl, or nitro substituents; providing that said alkyl groups or phenyl groups are more desirable than the other groups mentioned.

Examples of the primary amine particularly useful as the raw material for the maleinamic acid in this invention include methylamine, ethylamine, n-propylamine, isopropylamine, n-butylamine, sec-butylamine, isobutylamine, tert-butylamine, n-hexylamine, n-dodecylamine, allylamine, benzylamine, cyclohexylamine, aniline, nitroaniline, aminomonochloroaniline, dichloroaniline, toluidines, xylidines, and ethylanilines.

Synthesis of a maleinamic acid proceeds virtually stoichiometrically. For example, the maleinamic acid can be synthesized by causing the amine in an amount of 0.8 to 1.5 mols, preferably 0.9 to 1.2 mols, to react upon each mol of maleic anhydride.

The organic non-polar solvent to be used in the present invention is preferable to be capable of permitting the water formed by the reaction of dehydration and cyclization to be expelled from the reaction system through azeotropic distillation therewith, insoluble or immiscible in water, inert, and incapable of participating in the reaction. Examples of the organic solvent meeting this description are benzene, toluene, oil fractions boiling at temperatures in the range of 50° to 120° C., xylenes, ethyl benzene, isopropyl benzene, cumene, mesitylene, tert-butyl benzene, pseudo-cumene, trimethyl hexane, octane, tetrachloroethane, nonane, chlorobenzene, ethyl cyclohexane, oil fractions boiling at temperatures in the range of 120° to 170° C., m-dicyclobenzene, sec-butyl benzene, p-dichlorobenzene, decane, p-cymene, o-dichlorobenzene, butyl benzene, decahydronaphthalene, tetrahydronaphthalene, dodecane, naphthalene, cyclohexyl benzene, and oil fractions boiling at temperatures in the range of 170° to 250° C. From the standpoint of enabling this reaction to proceed smoothly under satisfactorily economic conditions, the amount of this solvent to be used in the reaction is in the range of about 1 to about 20 times, preferably 3 to 7 times (by volume), the amount of maleimic acid.

Further, the solvent is selected on the condition that it should possess a boiling point suiting the prevalent reaction conditions in due consideration of the solubility of the maleimide, price, and ease of handling. When the separation of the maleimide and the solvent after completion of the reaction demands an important consideration, there are times when the reaction performed by the use of a solvent of a low boiling point under application of pressure may prove to be more advantageous.

As a catalyst, there is used an amine salt which is obtained by subjecting an inorganic or organic monobasic or polybasic acid such as p-toluenesulfonic acid, orthophosphoric acid, metaphosphoric acid, pyrophosphoric acid, benzene sulfonic acid, or trichloroacetic acid with an amine as a raw material for the production of maleimide. This amine salt is preferred to be such that at least one of the protons of the monobasic acid or polybasic acid is substituted with an amine.

As the catalyst, a mixture of the amine salt with the inorganic or organic acid can also be used. This mixed catalyst produces desirable results when the amine salt content thereof at least exceeds 40 mol %, preferably falls in the range of 50 to 80 mol %.

Further as the catalyst, what is obtained by supporting on a solid carrier either the amine salt or a mixture of the amine salt just mentioned with the inorganic or organic acid can be effectively used. Furthermore, when the catalyst is supported on the solid carrier, the amine content may be zero percent. That is to say, sole acid catalyst may be used.

The amount of the catalyst to be used falls in the range of about 2 to about 400 mol %, preferably 20 to 200 mol %, as an acid component contained in the catalyst, based on the amount of the maleinamic acid, wherein the acid component contained in the catalyst means both an acid component which constitutes the amine salt and free acid.

Examples of the solid carrier to be used advantageously herein include natural minerals such as kaolins, clay, talc, chalk, quartz, bentonite, montmorillonite, and diatomaceous earth; synthetic minerals such as highly dispersed silicic acid, alumina, silicates, activated carbon, gypsum, iron oxide red, titanium dioxide, silica, silica-alumina, and zirconium oxide; and natural rocks such as calcite, marble, pumice, sepiolite, and dolomite.

Such an inorganic carrier is used in the form of powder, in the form of granules obtained by pelletizing and classifying the relevant substance, or in the form of a honeycomb.

It is also permissible to use an organic carrier. A granular carrier of polyfluorocarbon, polystyrene, or phenol resin can be effectively used. The catalysis is obtained with particularly desirable results when the carrier is made of such a porous substance as diatomaceous earth, silica gel or activated carbon. As typical examples of the cmmercially available carrier usable effectively herein include a product of diatomaceous earth (marketed by Showa Chemical Industry Co., Ltd. under trademark designation of "Radiolight") and products of silica gel (marketed by Fuji-Davison Chemical Co., Ltd. under trademark designations of "Carriact" "SYLOID," and "Microbead Silica Gel"), a product of silica gel (marketed by Wako-Junyaku Industry Co., Ltd. under trademark designation of "Wakogel"), and a product of activated carbon (marketed by Taiyo Kaken Co., Ltd. under trademark designation of "BAC".

Though the amount of the carrier-supported catalyst to be used is variable with the physical properties of the carrier used therein, it is generally in the range of 0.5 to 500% by weight, desirably 5 to 200% by weight, and particularly desirably 10 to 100% by weight, based on the amount of the carrier.

As means for supporting the catalyst on the carrier, any of the conventional methods such as the immersion method and the spray can be adopted. The catalyst may be supported directly on the carrier or it may be supported in an organic solvent or an aqeous solution.

When the amine salt obtained by the reaction of neutralization of the amine as the raw material with an acid is used as the catalyst either independently or in a form mixed with an acid, the acid catalyst may be supported first on the carrier and then caused to react with the amine or the amine salt or the mixture of the amine salt with an acid may be prepared in advance and subsequently supported on the carrier. It is provided, however, that when the amine salt is used by itself, since the amine salt is solid at normal room temperature, it must be supported on the carrier in the form of an aqueous solution.

The amount of the catalyst of the foregoing description to be used is in the range of about 2 to about 400 mol %, preferably 20 to 200 mol %, based on the amount of the maleinamic acid to be contained as an acid component, part or the whole of the acid destined to serve as the catalyst may be neutralized with an amine.

In the reaction of neutralization, the reaction may be carried out in the presence of a metal-containing compound and a stabilizer when occasion demands.

The amine salt produced as described above or the mixture of the amine salt with an acid is insoluble in the organic solvent to be used in the present invention. In the reaction system, therefore, this liquid catalyst assumes a state separated into the two layers, an organic layer and an inorganic layer. This state remains intact during and after the reaction. Moreover, the amine salt or the mixture thereof with an acid serving as the catalyst remains substantially unchanged before and after the reaction. The catalyst system of this nature itself, therefore, can be utilzied in situ in the next cycle of reaction without being recovered and refined in the meantime.

When this catalyst layer is to be used in the next cycle of reaction, the organic layer and the catalyst layer existing at the end of the reaction may be separated one from the other at a temperature in the range of 120° to 250° C., and the catalyst layer consequently recovered may be put to use directly in the next cycle of reaction. Otherwise, the recovered catalyst layer may be diluted with 5 to 20% by weight of water to lower both temperature and viscosity so to be added to the reaction system for the next cycle of reaction for the sake of convenience of handling.

As concerns the manner of use of the supported catalyst of the foregoing description, the catalyst may be used as added in the form of powdered catalyst to a stirring type reaction kettle or it may be used as granulated and packed in the form of a fixed bed in a flow type reaction tube.

There are times when the reaction can be carried out, as disclosed in U.S. Pat. No. 4,623,734, in the presence of a metal-containing compound and a stabilizer. The metal-containing compound to be used in this case is selected from among oxides, acetates, maleates, succinates, nitrates, phosphates, chlorides, and sulfates of at least one metal selected from the group consisting of zinc, chromium, palladium, cobalt, nickel, iron, and aluminum. Among other compounds enumerated above, zinc acetate proves to be particularly effective. The amount of the metal-containing compound to be used is in the range of 0.005 to 0.5 mol %, preferably 0.01 to 0.1 mol %, as metal, based on 1 mol of the maleinamic acid.

Examples of the stabilizer to be used advantageously herein include methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic esters, mercaptobenzimidazole, triphenyl phosphite, alkylphenols, and alkylbisphenols.

The stabilizer plays the part of enabling the maleimide which is produced by the reaction of imidation to retain stably during the course of the imidation without being degenerated at the elevated temperature of the reaction.

Concerning the amount of the stabilizer to be added, the addition of the stabilizer in a minute amount is not sufficiently effective and the addition thereof in an unduly large amount is undesirable because it entails the drawback that the excess of stabilizer finds its way into the final product. The amount of the stabilizer to be effectively used is in the range of 0.005 to 0.5 mol %, preferably 0.05 to 0.3 mol %, based on 1 mol of the maleinamic acid.

Regarding the manner of working out the present invention, first maleic anhydride prepared as a solution in an organic solvent and an amine compound added thereto are allowed to react with each other at a temperature not exceeding 150° C., preferably falling in the range of 30° to 120° C., for a period of 15 to 120 minutes, preferably 30 to 60 minutes to produce maleinamic acid. Then, the reaction system in which the maleinamic acid is left unisolated, the catalyst or the catalyst layer separated from the reaction system of the preceding cycle of reaction, and optionally the metal-containing compound and/or the stabilizer are combined and heated at a temperature in the range of 120° to 250° C., preferably 130° to 220° C., for a period in the range of one hour to 15 hours, preferaby 3 to 7 hours to effect the reaction in a continuous pattern with the formed water expelled from the system through azeotropic distillation or to effect the reaction in a batchwise pattern with the expulsion of the formed water carried out at the end of the reaction. As the result, the maleimide is produced in a high yield.

The maleimide which is consequently obtained is a compound represented by the general formula II, for example.

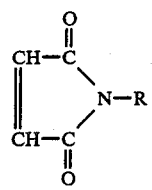

wherein R has the same meaning as defined above. Typical examples of the maleimides include N-methyl maleimide, N-ethyl maleimide, N-n-propyl maleimide, N-isopropyl maleimide, N-n-butyl maleimide, N-sec-butyl maleimide, N-tert-butyl maleimide, N-n-hexyl maleimide, N-n-dodecyl maleimide, N-allyl maleimide, N-benzyl maleimide, N-cyclohexyl maleimide, N-phenyl maleimide, N-nitrophenyl maleimide, N-hydroxyphenyl maleimide, N-methoxyphenyl maleimide, N-ehoxyphenyl maleimide, N-monochlorophenyl maleimide, N-dichlorophenyl maleimide, N-monomethylphenyl maleimide, N-dimethylphenyl maleimide, and N-ethylphenyl maleimide. Of course, the maleimides which this invention is intended to embrace are not limited to the examples cited above.

This invention which has been described above brings about the following advantages.

(1) The present invention permits a maleimide of high purity to be produced in a high yield, because the amine salt formed by the reaction of neutralization of the amine as the raw material for the production of the maleimide with an inorganic or organic monobasic or polybasic acid or the mixture of the amine salt with an acid possesses a catalytic activity of high selectivity on the reaction of cyclizing imidation.

(2) The cost of the catalyst can be substantially disregarded because the amine salt or the mixture used as the catalyst is stable enough to be used time and again in the successive cycles of reaction.

(3) Since the catalyst is used repeatedly, there is substantially no need for the treatment otherwise required to be given to the used catalyst for the eventual prevention of environmental pollution. Since the reaction system, therefore, can be operated in a closed pattern, there is virtually no possibility of the environment being polluted with discarded catalyst.

When the solid catalyst supported on the carrier is used, this invention brings about the following advantages.

(4) This invention permits a maleimide of high purity to be produced in a high yield because the catalyst system produced by supporting on a solid carrier the amine salt obtained from the acid and the amine as the raw material and/or the acid possesses a catalytic activity of high selectivity on the reaction of ring-closure imidation.

(5) Since the catalyst is supported on the solid carrier and, therefore, the separation of the reaction solution and the catalyst can be easily effected, the reaction can be easily carried out in a continuous pattern and, what is more, the productivity of the process can be enhanced to a great extent.

(6) Since the catalyst is lost only nomically, the cost of the catalyst can be substantially disregarded.

As described in (1) through (3) and, when the catalyst deposited on the solid catalyst is used, further in (4) through (6) above, this invention permits a maleimide to be easily produced inexpensively and safely.

Now, the present invention will be described more specifically below with reference to working examples.

EXAMPLE 1

In a Meyer's flask having an inner volume of 300 ml, 100 g of orthoxylene and 60 g of sulfuric acid were dispersed. Then the Meyer's flask was kept cooled in a water bath, 122 g of cyclohexylamine was added dropwise thereto to obtain a xylene slurry of white crystals of dicyclohexylamine salt of sulfuric acid.

Separately, a flask provided with a condenser incorporating therein a water separator, a dropping funnel, and a stirrer was charged first with 100 g of orthoxylene and then with 100 g of maleic anhydride and heated until the inner temperature thereof reached 100° C. to effect dissolution of maleic anhydride.

Then, a solution of 100 g of cyclohexylamine in 600 g of orthoxylene was added dropwise to the solution while in a stirred state over a period of one hour to synthesize a slurry of N-cyclohexyl maleinamic acid in the solvent.

Thereafter, this slurry and the slurry of amine salt were wholly combined and then left reacting for two hours by being heated and stirred at 147° C., with the water formed by the reaction continuously expelled from the reaction system through distillation in combination with the solvent. After the reaction was completed, the catalyst layer separated in a lower layer from the reaction solution at 147° C. was removed.

Subsequently, the reaction solution was cooled to 60° C. and washed by 30 minutes' stirring with 100 g of water. The water layer consequently formed was separated from the washed reaction solution. This operation repeated twice. Then, the remaining organic layer was distilled under a vacuum of 10 mmHg (abs) to expel the solvent therefrom.

Then, the contents of the flask and 0.3 g of copper dibutyl dithiocarbamate newly added thereto were kept under a vacuum of 5 mmHg (abs) at a flask interior temperature of 130° to 150° C. for 30 minutes to effect distillation of N-cyclohexyl maleimide. As the result, 168 g of bright white crystals of N-cyclohexyl maleimide were obtained. The purity of this product was 99.9% by weight. The yield of this product was 92.8 mol % based on cyclohexylamine used as the raw material.

A reaction was carried out by faithfully following the procedure described above, excepting the catalyst layer separated from the reaction system of the preceding cycle of reaction was used instead. Consequently, there were obtained 169 g of bright white crystals of N-cyclohexyl maleimide. The purity of this product was 99.8% by weight and the yield thereof was 93.3 mol % based on cyclohexylamine used as the raw material.

EXAMPLE 2

In a Meyer's flask having an inner volume of 300 ml, 100 g of orthoxylene and 60 g of orthophosphoric acid were dispersed. Then, the Meyer's flask was kept cooled in a water bath and 61 g of cyclohexylamine was added dropwise thereto obtain a xylene slurry solution of white crystals of monocyclohexylamine salt of orthophosphoric acid.

Separately, a flask provided with a condenser incorporating therein a water separator, a dropping funnel and a stirrer was charged first with 100 g of orthoxylene and then with 100 g of maleic anhydride and heated until the inner temperature of the flask reached 100° C., to effect dissolution of maleic anhydride.

Then, a solution of 100 g of cyclohexylamine in 600 g of orthoxylene was added dropwise while in a stirred state over a period of one hour to synthesize a slurry solution of N-cyclohexyl maleinamic acid in orthoxylene.

Then, this slurry and the slurry of amine salt were wholly added. The resultant mixture and 0.1 g of copper dibutyl dithiocarbamate added thereto were left reacting for seven hours by being heated and stirred at 143° C., with the water formed by the reaction expelled from the reaction system in combination with orthoxylene in the meantime. After the reaction was completed, the catalyst layer separated in a lower layer from the reaction solution at 143° C. was removed.

Subsequently, the reaction solution was cooled to 60° C. and washed by 30 minutes' stirring with 100 g of water, to separate the water layer from the reaction solution. This operation was repeated twice. The organic phase consequently obtained was distilled under a vacuum of 10 mmHg (abs) to expel ortho-xylene.

Then, the contents of the flask and 0.3 g of copper dibutyl dithiocarbamate newly added thereto were kept under a vacuum of 5 mmHg (abs) at an inner flask temperature of 130° to 150° C. for 30 minutes to effect distillation of N-cyclohexyl maleimide. As the result, there were obtained 163 g of bright white crystals of N-cyclohexyl maleimide. The purity of this product was 99.8% by weight and the yield thereof was 90.0 mol % based on cyclohexyl amine used as the raw material.

A reaction was carried out by faithfully repeating the procedure described above, excepting the catalyst layer separated from the reaction system of the preceding cycle of reaction was used instead. Consequently, there were obtained 164 g of bright white crystal of N-cyclohexyl maleimide. The purity of this product was 99.8% by weight and the yield thereof was 90.6 mol % based on cyclohexylamine used as the raw material.

EXAMPLE 3

In a Meyer's flask having an inner volume of 300 ml, 100 g of P-cymene and 10 g of orthophosphoric acid were dispersed. Then, the Meyer's flask was kept cooled in a water bath and 9.5 g of aniline was added dropwise thereto, to obtain a slurry of white crystals of monoaniline salt of orthophosphoric acid.

Separately, a galss flask having an inner volume of 1 liter was fitted with a thermometer, a stirrer, and a water separator.

Then, a solution of 53 g of powdered maleic anhydride in 50 g of P-cymene was placed in the glass flask. The flask was adjusted to an inner temperature of 130° C. and a solution of 50 g aniline in 400 g of p-cymene was added piecemeal thereto over a period of 30 minutes, to synthesize a slurry solution of N-phenyl maleinamic acid.

The slurry solution thus obtained and the whole of the amine salt slurry, 0.034 g of zinc acetate, and 0.065 g of p-methoxyphenol added thereto were left reacting at a temperature of 180° C. for three hours, with the water formed therein expelled from the reaction solution through distillation in combination with p-cymene. Thereafter, the reaction solution was cooled to 30° C., washed with water, and distilled under a vacuum to expel p-cymene. Consequently, there were obtained 94.0 g of crystals of N-phenyl maleimide. The purity was found by liquid chromatography to be 93.7% by weight. The yield of the product was 94.7 mol % based on amine.

A reaction was carried out by faithfully repeating the procedure described above, excepting the catalyst layer separated from the reaction system of the preceding cycle of reaction. As the result, there were obtained 95.0 g of crystals of N-phenyl maleimide.

The purity of this product was found by liquid chromatography to be 93.2% by weight. The yield thereof was 95.2 mol % based on amine.

CONTROL 1

To a solution of 98 g of maleic anhydride in 500 g of toluene, 99.2 g of cyclohexylamine was added dropwise at a temperature in the range of 50° to 70° C. while in a stirred state. After the dropwise addition, the resultant mixture was stirred for two hours. Consequently N-cyclohexyl maleinamic acid was obtained. Then, the reaction solution and 14 g of methanesulfonic acid, 8.7 g of methanesulfonic acid-N-cyclohexyl maleinamate, and 15 g of N-methyl pyrrolidone added thereto were left reacting at 115° C. for 3.5 hours in a refluxed state, with the formed water continuously expelled from the reaction system through azeotropic distillation with toluene.

Then, the resultant reaction solution was caused to react with 15 g of acetic anhydride for 30 minutes, cooled to 60° C., and filtered to be deprived of insoluble impurities, the catalyst, and unaltered N-cyclohexyl maleinamic acid. Subsequently, the filtrate was washed by 30 minutes' stirring with 200 g of water to separate the water layer. This operation was repeated twice. The organic layer consequently obtained was distilled under a vacuum of 30 mmHg (abs) to expel toluene. As the result, there was obtained 172 g of a brown solid containing cyclohexyl maleimide. By the GPC analysis, the N-cyclohexyl maleimide was found to be 10.0% by weight and the yield of N-cyclohexyl maleimide was to be 9.6 mol %, based on cyclohexylamine. When the reaction solution was analyzed by gas chromatography, the results showed the same yield.

CONTROL 2

A reaction was carried out by faithfully repeating the procedure of Control 1, excepting 73 g of N-butylamine was used in the place of cyclohexylamine, 14 g of methanesulfonic acid and 8.4 g of tributylamine salt of methanesulfonic acid were used as a reaction catalyst, and dimethyl formamide was used in the place of N-methyl pyrrolidone as the polar solvent. Consequently, there was obtained 151 g of a brown oily liquid containg N-n-butyl maleimide.

By the GPC analysis, the content of N-n-butyl lmaleimide was found to be 13.4% by weight and the yield thereof to be 13.2 mol % based on N-butylamine used as the raw material.

When the reaction solution was washed with water and analyzed by gas chromatography, the results showed the same yield.

CONTROL 3

A solution of 43.1 g of maleic anhydride in 331.8 g of chlorobenzene and 39.7 g of cyclohexylamine added thereto were left reacting at 40° C. for one hour.

The slurry solution of N-cyclohexyl maleinamic acid consequently obtained and 12 ml of dimethyl acetamide and 2 g of trichloroacetic acid added thereto were left reacting at 135° C. for six hours, with the formed water continuously expelled in combination with the solvent from the reaction system in the meantime.

At the end of the reaction, there was obtained 402 g of reaction solution. This reaction solution, on analysis by gas chromatography, was found to contain 2.2% by weight of N-cyclohexyl maleimide.

The yield of this N-cyclohexyl maleimide was 12.3 mol %, based on cyclohexylamine used as the raw material.

EXAMPLE 4

In a Meyer's flask having an inner volume of 300 ml, 100g of oxoxylene and 60 g of orthophosphoric acid were dispersed. Then, the Meyer's flask was kept cooled in a water bath and 37 g of cyclohexylamine was added dropwise thereto to obtain a slurry solution of a white mixed catalyst of monocyclohexylamine salt of orthophosphoric acid and orthophosphoric acid in xylene. The amine salt content in the mixed catalyst was 60.9 mol %.

Separately, a flask provided with a condenser indorporating therein a water separator, a dropping funnel, and a stirrer was charged first with 100 g of orthoxylene and then with 100 g of maleic anhydride and heated until the inner temperature thereof reached 100° C., to dissolve the maleic anhydride.

Then, a solution of 100 g of cyclohexylamine in 600 g of orthoxylene was added dropwise while in a stirred state over a period of one hour, to synthesize a slurry solution of N-cyclohexyl maleinamic acid in orthoxylene.

Thereafter, this slurry solution and the mixed slurry solution of amine salt and orthophosphoric acid (the amount of the mixed catalyst corresponding to 60.7 mol %, based on maleinamic acid) and 0.1 g of copper dibutyl dithiocarbamate added thereto were left reacting for seven hours by being heated and stirred at 143° C., with the water formed by the reaction continuously expelled by distillation in combination with orthoxylene from the reaction system in the meantime. After the reaction was completed, the catalyst layer separated in a lower layer from the reaction solution at 143° C. was removed.

Subsequently, the reaction solution was cooled to 60° C. and washed by being stirred with 100 g of water for 30 minutes, to separate the water layer. This operation was repeated twice. The organic layer consequently formed was distilled under a vacuum of 10 mmHg (abs) to expel oroxylene.

Then, the contents of the flask and 0.3 g of copper dibutyl dithiocarbamate newly added were left standing under a vacuum of 5 mmHg (abs) at a flask inner temperature of 130° to 150° C. for 30 minutes, to effect distillation of N-cyclohexyl maleimide. As the result, there were obtained 171 g of bright white crystals of N-cyclohexyl maleimide. The purity of this product was 99.8% by weight and the yield thereof was 94.4 mol % based on cyclohexylamine used as the raw material.

Thereafter, a reaction was carried out by faithfully following the procedure described above, excepting the catalyst layer separated from the reaction system of the preceding cycle of reaction was used instead. Consequently, there were obtained 171 g of bright white crystals of N-cyclohexyl maleimide. The purity of this product was 99.8% by weight and the yield thereof was 94.4 mol % based on cyclohexyl amine used as the raw material.

EXAMPLE 5

In a Meyer's flask having an inner volume of 300 ml, 100 g of p-cymene and 100 g of orthophosphoric acid were dispersed. Then, the Meyer flask was kept cooled in a water bath and 56 g of n-butyl amine was added drowpwise thereto, to obtain a white mixed slurry solution of n-butylamine salt of orthophosphoric acid and orthophosphoric acid. The amine content in this mixed catalyst was 75.0 mol %.

Separately, a reactor was prepared by furnishing a glass flask having an inner volume of 1 liter with a thermometer, a stirrer, and a water separator.

Then, a solution of 53 g of powdered maleic anhydride in 50 g of p-cymene was placed in the reactor. Subsequently, the inner temperature of the reactor was adjusted to 130° C. and a solution of 40 g of n-butyl amine in 400 g of p-cymene was added thereto piecemeal in a dropwise manner over a period of 30 minutes, to synthetize a slurry solution of N-(n-butyl)maleinamic acid.

The slurry solution thus obtained and the slurry solution of mixed catalyst (the amount of mixed catalyst corresponding to 186.5 mol % based on the maleinamic acid), 0.034 g of zinc acetate, and 0.065 g of p-methoxy phenol added thereto were left reacting at a temperature of 180° C. for three hours, with the formed water continuously expelled in combination with p-cymene form the reaction system in the meantime. After the reaction was completed, the reaction solution weighed 620 g. The concentration of N-(n-butyl) maleimide in this reaction solution was 11.5% by weight. The yield of the maleimide was 85.1 mol % based on n-butylamine used as the raw material.

A reaction was carried out by faithfully repeating the procedure described above, excepting the catalyst layer separated from the reaction system of the preceding cycle of reaction was used instead, to obtain 625 g of a reaction solution. The concentration of N-(n-butyl) maleimide in this reaction solution was found by analysis to be 11.6% by weight. The yield was 86.5 mol %.

EXAMPLE 6

In a Meyer's flask having an inner volume of 300 ml, 60 g of orthophosphoric acid was placed. Then, this Meyer's flask was kept cooled in a water bath and 46 g of cyclohexylamine was added dropwise thereto, to obtain a viscous slurry solution of mixed catalyst of cyclohexyl-monoamine of phosphoric acid and phosphoric acid. The content of amine salt in this mixed catalyst was 75.8 mol %.

Separately, a glass autoclave having an inner volume of 1 liter and provided with a thermoneter, a condenser, a dropping funnel, and a stirrer was charged first with 100 g of orthoxylene and then with 100 g of maleic anhydride and then heated until the inner temperature of the flask reached 100° C., to effect dissolution of the maleic anhydride.

Subsequently, a solution of 100 g of cyclohexylamine in 400 g of orthoxylene was added dropwise thereto while in a stirred stste over a period of 30 minutes, to synthesize a slurry solution of N-cyclohexyl maleinamic acid in the solvent.

Then, the slurry solution and the slurry of mixed catalyst (the amount of the mixed catalyst corresponding to 60.7 mol % based on the maleinamic acid added thereto were left reacting at an inner of 152° C. for three hours in a closed system without expulsion of the formed water. In the reaction system, the inner pressure was 1.2 atm at the outset of the reaction and was 7.0 atm after three hours of the reaction.

After the reaction was completed, the inner temperature was adjusted to 130° C. and then the inner pressure was allowed to fall to normal atmospheric pressure. The reaction product was removed from the autoclave and left standing at rest. Consequently, the reaction solution was separated clearly into two layers, i.e. an organic layer and a catalyst layer. The organic layer weighed 660 g. The content of N-cyclohexyl maleimide in this organic layer, on analysis by gas chromatography, was found to be 24.6% by weight. The yield of this maleimide was 89.8 mol %, based on cyclohexylamine used as the raw material.

Subsequently, a reaction was carried out by faithfully repeating the procedure described above, excepting the mixed catalyst layer of amine salt and acid separated from the reaction system of the preceding cycle of reaction was used instead. Consequently, there was obtained 664 g of an organic layer. The content of N-cyclohexyl maleimide in this organic layer was 24.5% by weight. The yield thereof was 90.0 mol % based on cyclohexylamine used as the raw material.

EXAMPLE 7

In a beaker having an inner volume of 200 ml, 20 g of orthophosphoric acid was placed and then 30 g of diatomaceous earth (product of Showa Chemical Industry Co., Ltd. marketed under trademark designation of "Radiolight #200) was added thereto to effect deposition of the orthophosphoric acid on the diatomaceous earth.

A flask provided with a thermometer, a condenser incorporating therein a water separator, a dropping funnel, and a stirrer was charged with a solution of 55 g of maleic anhydride in 50 g of xylene. Then, the inner temperature of the flask was adjusted to 80° C. and a solution of 50 g of aniline in 400 g of xylene was added piecemeal thereto over a period of 30 minutes, to synthesize a slurry solution of N-phenyl maleinamic acid in xylene.

The slurry solution thus obtained and the catalyst prepared in the beaker in advance were left reacting at 140° C. for three hours. After the reaction was completed, the reaction solution was separated from the catalyst layer. It was then cooled to 80° C., washed with water, and thereafter distilled under a vacuum to expel xylene and obtain 83 g of crystals of N-phenyl maleimide. The purity of the crystals, on analysis by liquid chromatography, was found to be 87.4% by weight. The yield of this product was 78.0% based on aniline used as aniline.

EXAMPLE 8

The procedure of Example 7 was faithfully repeated, excepting 0.034 g of zinc acetate and 0.01 g of copper dibutyl dithiocarbamate were added instead during the course of imidation. As the result, there were obtained 93 g of crystals of N-phenyl maleimide. The purity of the crystals, on analysis by liquid chromatography, was found to be 94.3% by weight. The yield thereof was 94.3 mol % based on aniline used as the raw material.

EXAMPLE 9

In a Meyer's flask having an inner volume of 300 ml, 100 g of xylene and 20 g of orthophosphoric acid were dispersed. Then, the same diatomaceous earth as used in Example 7 was introduced therein to effect deposition of the orthophosphoric acid on the diatomaceous earth. Then it was reacted with 9.5 g of aniline. The procedure of Example 8 was repeated, excepting the deposited catalyst mentioned above was used as a catalyst for the imidation. Consequently, there were obtained 92 g of crystals. The purity of the crystals, on analysis by liquid chromatography, was found to be 98.5% by weight. The yield thereof was 97.5 mol % based on aniline used as the raw material.

After the reaction was completed, in the reactor containing the used catalyst intact, a total of 20 cycles of the imidation were carried out. The yield of reaction in the 20th cycle was 98.1 mol %. The catalyst after the 20th cycle of reaction showed the same attributes as the catalyst after the first cycle of reaction.

CONTROL 4

The procedure of Example 7 was repeated, excepting the orthophosphoric acid was not deposited on diatomaceous earth. As the result, there were obtained 82 g of crystals of N-phenyl maleimide. The purity of the crystals, on analysis by liquid chromatography, was found to be 74.8% by weight. The yield of the product was 66.0 mol %, based on aniline used as the raw material.

CONTROL 5

The procedure of Example 8 was repeated, excepting the orthophosphoric acid was not deposited on diatomaceous earth. Consequently, there were obtained 85 g of crystals of N-phenyl maleimide. The purity of the crystals, on analysis by liquid chromatography, was found to be 90.2% by weight. The yield of this product was 80.5 mol % based on aniline used as the raw material.

CONTROL 6

The procedure of Example 9 was repeated, excepting the orthophosphoric acid was not deposited on diatomaceous earth. Consequently, there were obtained 90 g of crystals of N-phenyl maleimide. The purity of the crystals, on analysis by liquid chromatography, was found to be 91.7% by weight. The yield of this product was 88.8 mol % based on aniline used as the raw material.

EXAMPLE 10

In a meyer's flask having an inner volume of 300 ml, 60 g of orthophosphoric acid was placed and stirred with 60 g of a granular silica gel carrier (product of Fuji-Davison chemical Co., Ltd. marketed under trademark designation of "Carriact-30") to effect deposition of the acid on the carrier.

Subsequently, 100 g of orthoxylene was added thereto and the Meyer's flask was kept cooled in a water bath and 37 g of cyclohexylamine was added dropwise thereto, to effect partial conversion of the carried acid into an amine salt.

Separately, a flask provided with a thermometer, a condenser indorporating therein a water separator, a dropping funnel, and a stirrer was charged first with 100 g of orthoxylene and then with 100 g of maleic anhydride and heated to an inner temperature of 100° C., to effect dissolution of the maleic anhydride.

Subsequently, a solution of 100 g of cyclohexylamine in 600 g of orthoxlene was added dropwise in a stirred state over a period of one hour, to synthesize a slurry solution of N-cyclohexyl maleinamic acid in orthoxylene.

Then, the slurry solution and the carried catalyst and 0.1 g of copper dibutyl dithiocarbamate added thereto were left reaction for seven hours by being heated and stirred at 143° C., with the water formed by the reaction continuously expelled by distillation in combination with the oroxylene from the reaction system in the meantime.

After the reaction was completed, the reaction solution was analyzed for N-cyclohexyll maleimide by gas chromatography. Thus, the yield of N-cyclohexyl maleimide was found to be 97.8 mol % based on cyclohexyl amine used as the raw material.

EXAMPLE 11

In a beaker having an inner volume of 500 ml, 100 g of sulfuric acid and 200 g of silica gel (product of Wako Junyaku marketed under trademark designation of "Wako Gel C100") were stirred to effect support of the acid on the silica gel. Separately, a reactor was prepared by furnishing a glass flask having an inner volume of 1 liter with a thermometer, a stirrer, and a water separator. Then, a solution of 53 g of powdered maleic anhydride in 50 g of p-cymene was placed in the reactor. Subsequently, the inner temperature of the reactor was adjusted to 130° C. and a solution of 40 g of n-butylamine in 400 g of p-cymene was added piecemeal thereto in a dropwise manner over a period of 30 minutes, to synthesize a slurry solution of N-(n-butyl) maleinamic acid.

The slurry solution thus obtained and the supported catalyst, 0.034 g of zinc acetate, and 0.065 g of p-methoxyphenol added thereto were left reacting at 180° C., with the formed water continuously expelled in combination with the p-cymene from the reaction system in the meantime.

After the reaction was completed, the reaction solution was analyzed for the concentration of N-(n-butyl) maleimide. As the result, the yield of the product was found to be 80.4 mol %.

CONTROLS 7-10

A flask provided with a condeser incorporating therein a water separator, a dropping funnel, and a stirrer was charged first with 100 g of orthoxylene and then with 100 g of maleic anhydride and heated until the inner temperature thereof reached 100° C. to effect dissolution of maleic anhydride.

Then, a solution of 100 g of cyclohexylamine in 600 g of orthoxylene was added dropwise to the solution while in a stirred state over a period of one hour to synthesize a slurry of N-cyclohexyl maleinamic acid in the solvent.

Thereafter, catalysts shown in Table 1 were added to the slurry respectively and then left reacting for two hours tby being heated and stirred at 147° C., with the water formed by the reaction continuously expelled from the reaction system through distillation in combination with orthoxylene. After the reaction, N-cyclohexyl maleimide ontent was determined by gas chromatography to obtain reaction yield. The results are shown in Table 1.

TABLE 1

| Controls | Catalyst (molar ratio) | Polar solvent | Acid (mol % as acid to amine) | Yield (mol % to amine) |
|---|---|---|---|---|
| 7 | H$_2$SO$_4$/DMF (1:1) | 36 g | 60 g (60.7%) | 32 |
| 8 | H$_2$SO$_4$/DMF (1:2) | 72 g | 60 g (60.7%) | 28 |
| 9 | OPA/DMF (1:1) | 36 g | 60 g (60.7%) | 44 |
| 10 | OPA/DMSO (1:1) | 48 g | 60 g (60.7%) | 29 |

*DMF: dimethyl formamide
DMSO: dimethyl sulfoxide
OPA: orthophosphoric acid

What is claimed is:

1. A method for the production of a maleimide of formula II:

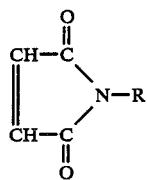

wherein R is a member selected from the group consisting of alkyl of 1–20 carbon atoms, phenyl, benzyl, cyclohexyl, pyridyl, quinolyl and the said moieties when substituted by halogen, carboxyl or nitro which comprises the sequential steps of (a) reacting maleic anhydride with a primary amine of the formula NH$_2$-R wherein R is as defined above to form the corresponding maleinamic acid and (b) heating said maleinamic acid in a water insoluble or water immiscible inert non-polar organic solvent said solvent being utilized in a ratio by volume of from about 1 to about 20 to 1 with respect to said maleinamic acid in the presence of a primary amine acid addition salt catalyst, in an amount of about 2 to about 400 mol % of acid addition component, based on said maleinamic acid, formed from said primary amine and a strong inorganic or organic acid, said salt containing said acid addition component in an amount of less than 60 mol %, at a temperature of from about 120° to 250° C. and continuously distilling off the thus formed water as a mixture with said solvent.

2. A method according to claim 1, wherein the amount of said catalyst to be used is in the range of 20 to 200 mol %, as an acid component contained in said catalyst, based on said maleinamic acid.

3. A method according to claim 1, wherein said acid is at least one member selected from the group consisting of sulfuric acid, p-toluenesulfonic acid, orthophosphoric acid, methaphosphoric acid, pyrophosphoric acid, benzenesulfonic acid, and trichloro-acetic acid.

4. A method according to claim 1, wherein the content of said inorganic or organic acid in said catalyst is in the range of 20 to 50 mol %.

5. A method for the production of a maleimide of formula II:

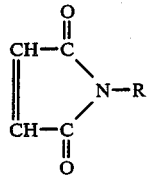

wherein R is a member selected from the group consisting of alkyl of 1–20 carbon atoms, phenyl, benzyl, cyclohexyl, pyridyl, quinolyl and the said moieties when substituted by halogen, carboxyl or nitro which comprises the sequential steps of:

(a) reacting maleic anhydride with a primary amine of the formula NH$_2$-R wherein R is as defined above to form the corresponding maleinamic acid and (b) heating said maleinamic acid in a water insoluble or water immiscible inert non-polar organic solvent said solvent being utilized in a ratio by volume of from about 1 to about 20 to 1 with respect to said maleinamic acid in the presence of a catalyst supported on a solid inert organic or inorganic carrier, said catalyst containing an acid component in an amount of about 2 to about 400 mol % of acid component, based on said maleinamic acid, at least one catalyst ingredient being selected from the group consisting of (a) a strong organic or inorganic acid, (b) an amine acid addition salt produced from said primary amine and a strong inorganic or organic acid, and (c) a mixture of said amine acid addition salt and a strong acid, at a temperature of from about 120° to 250° C. and continuously distilling off the thus formed water as a mixture with said solvent.

6. A method according to claim 5, wherein the amount of said catalyst ingredient to be suppported is the range of 0.5 to 500% by weight based on said carrier.

7. A method according to claim 5, wherein the said solid carrier is at least one member selected from the group consisting of diatomaceous earth, silica gel, and activated carbon.

8. A method according to claim 5, wherein the amount of said solvent to be used is in the range of 1 to 20 times by volume, based on the amount of said maleinamic acid.

9. A method for the production of a maleimide of formula II:

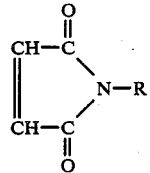

wherein R is a member selected from the group consisting of alkyl of 1–20 carbon atoms, phenyl, benzyl, cyclohexyl, pyridyl, quinolyl and the said moieties when substituted by halogen, carboxyl or nitro which comprises the sequential steps of:

(a) reacting maleic anhydride with a primary amine of the formula NH$_2$-R wherein R is as defined above to form the corresponding maleinamic acid, (b) heating said maleinamic acid in a water insoluble or water immiscible inert non-polar organic solvent, said solvent being utilized in a ratio by volume of from about 1 to about 20 to 1 with respect to said maleinamic acid in the presence of a metal containing compound selected from the group consisting of oxides, acetates, maleates, succinates, nitrates, phosphates, chlorides and sulfates of a metal selected from the group consisting of zinc, chromium, palladium, cobalt, nickel iron and aluminum and a stabilizer selected from the group consisting of methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic ester, mercaptobenzimidazole, triphenyl phosphite, alkylphenols and alkylbisphenols, and in the presence of said primary amine acid addition salt catalyst, in an amount of about 2 to about 400 mol % of acid addition component, based on said maleinamic acid, formed from said primary amine and a strong inorganic or organic acid, said salt containing said acid addition component in an amount of less than 60 mol % at a temperature of from about 120° to 250° C. and continuously distilling off the thus formed water as a mixture with said solvent.

10. A method according to claim 9, wherein said metal-containing compound is a zinc-containing compound.

11. A method according to claim 9, wherein said metal-containing compound is an acetate.

12. A method for the production of a maleimide of formula II:

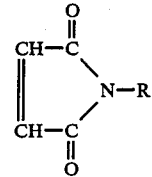

wherein R is a member selected from the group consisting of alkyl of 1-20 carbon atoms, phenyl, benzyl, cyclohexyl, pyridyl, quinolyl and the said moieties when substituted by halogen, carboxyl or nitro which comprises the sequential steps of:

(a) reacting maleic anhydride with a primary amine of the formula $NH_2$-R wherein R is as defined above to form the corresponding maleinamic acid, (b) heating said maleinamic acid in a water insoluble or water immiscible inert non-polar organic solvent, said solvent being utilized in a ratio by volume of from about 1 to about 20 to 1 with respect to said maleinamic acid in the presence of a metal containing compound selected from the group consisting of oxides, acetates, maleates, succinates, nitrates, phosphates, chlorides and sulfates of a metal selected from the group consisting of zinc, chromium, palladium, cobalt, nickel, iron and aluminum and a stabilizer selected from the group consisting of methoxy benzoquinone, p-methoxyphenol, phenothiazine, hydroquinone, alkylated diphenyl amines, methylene blue, tert-butyl catechol, tert-butyl hydroquinone, zinc dimethyldithiocarbamate, copper dimethyldithiocarbamate, copper dibutyldithiocarbamate, copper salicylate, thiodipropionic ester, mercaptobenzimidazole, triphenyl phosphite, alkylphenols and alkylbisphenols, and in the presence of a catalyst supported on a solid inert organic or inorganic carrier said catalyst containing an acid component in an amount of about 2 to about 400 mol % of acid component, based on said maleinamic acid, at least one catalyst ingredient being selected from the group consisting of (a) a strong organic or inorganic acid, (b) an amine acid addition salt produced from said primary amine and a strong inorganic or organic acid, and (c) a mixture of said amine acid addition salt and a strong acid at a temperature of from about 120° to 250° C. and continuously distilling off the thus formed water as a mixture with said solvent.

* * * * *